United States Patent [19]

Jähne

[11] Patent Number: 5,225,550

[45] Date of Patent: Jul. 6, 1993

[54] PROCESS FOR THE PREPARATION OF SUBSTITUTED ACYCLIC NUCLEOSIDES, AND INTERMEDIATES OCCURRING THEREIN

[75] Inventor: Gerhard Jähne, Frankfurt am Main, Fed. Rep. of Germany

[73] Assignee: Hoechst Aktiengesellschaft, Frankfurt am Main, Fed. Rep. of Germany

[21] Appl. No.: 720,698

[22] Filed: Jun. 25, 1991

[30] Foreign Application Priority Data

Jun. 27, 1990 [DE] Fed. Rep. of Germany ....... 4020481

[51] Int. Cl.$^5$ .................. C07D 473/18; C07D 473/34; C07D 251/16; C07D 239/46
[52] U.S. Cl. ......................... 544/277; 544/254; 544/264; 544/265; 544/276; 544/280; 544/243; 544/244; 544/299; 544/301; 544/302; 544/303; 544/304; 544/306; 544/309; 544/311; 544/312; 544/313; 544/314; 544/317; 546/22; 546/23; 546/118; 546/290; 546/300; 546/301; 546/302; 546/303
[58] Field of Search ............... 544/264, 265, 276, 277, 544/254, 309, 311–314, 317, 299, 301–304, 306; 546/22, 23, 118, 290, 300–303; 548/112, 113, 413 P, 252, 253, 255, 262.2, 267.2, 267.8, 268.2, 268.8, 342, 561, 562, 503, 504, 507, 333; 568/591, 600, 601, 602

[56] References Cited

U.S. PATENT DOCUMENTS

| | | | |
|---|---|---|---|
| 4,621,140 | 11/1986 | Verheyden et al. | 544/277 |
| 4,801,710 | 1/1989 | MacCoss et al. | 544/277 |
| 4,803,271 | 2/1989 | Verheyden et al. | 544/277 |
| 4,816,447 | 3/1989 | Ashton et al. | 544/277 |
| 4,826,981 | 5/1989 | Kobe et al. | 544/277 |
| 4,897,479 | 1/1990 | Tolman et al. | 544/277 |
| 4,931,575 | 6/1990 | Abushanab | 544/277 |
| 4,965,270 | 10/1990 | Harnden et al. | 544/277 |
| 5,017,701 | 5/1991 | Grinter et al. | 544/277 |
| 5,043,339 | 8/1991 | Beauchamp | 544/277 |
| 5,059,604 | 10/1991 | Krenitsky et al. | 544/277 |

FOREIGN PATENT DOCUMENTS

| | | |
|---|---|---|
| 0049072 | 4/1982 | European Pat. Off. . |
| 0152965 | 8/1985 | European Pat. Off. . |
| 0165164 | 12/1985 | European Pat. Off. . |
| 0217207 | 4/1987 | European Pat. Off. . |
| 0400686 | 12/1990 | European Pat. Off. . |
| 0450680 | 10/1991 | European Pat. Off. . |
| 2541681 | 8/1984 | France . |
| 2104070 | 3/1983 | United Kingdom ................ 544/277 |

OTHER PUBLICATIONS

Derwent Abstract of Priority Document No. 520,140, dated Feb. 25, 1983 of FR-A-2,541,681 published Aug. 31, 1984.
Derwent Abstract of Priority Documents of EP-A-0,217,207.
Chemical Abstracts, vol. 92, No. 5, Feb. 4, 1980, Abstract No. 41265h, Sokolowski.
W. T. Ashton et al., Biochem. Biophys. Res. Commun. 108, 1716-1721 (1982).
H. J. Schaeffer et al., Nature, 272, 583-585 (1978).
Houben-Weyl, Methods of Organic Chemistry, vol. VI/3, 203-213 (1965).
Winkelmann et al., CA106-213651g (1987).
Winkelmann et al., CA110-87985m (1989).
Winkler et al., CA 114-17132q (1991).
Mar., Adv. Org. Chem. 3rd Edition (1985) Reaction 6-6 pp. 789-791.

*Primary Examiner*—Cecilia Tsang
*Attorney, Agent, or Firm*—Finnegan, Henderson, Farabow, Garrett & Dunner

[57] ABSTRACT

It is possible, by using symmetrical formaldehyde acetals of the formula

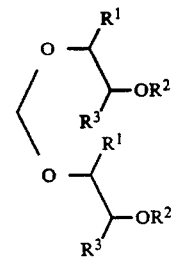

in which the substituents $R^1$–$R^3$ have the specified meanings, advantageously to introduce the substituent

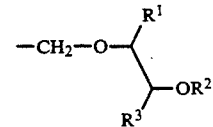

into nitrogen-containing heterocyclic systems to form acyclic nucleoside analogs.

8 Claims, No Drawings

PROCESS FOR THE PREPARATION OF SUBSTITUTED ACYCLIC NUCLEOSIDES, AND INTERMEDIATES OCCURRING THEREIN

DESCRIPTION

The present invention relates to a process for the preparation of substituted acyclic nucleosides and to intermediates occurring therein. Acyclic purine nucleosides such as 2-amino-9-[(1,3-bis-isopropoxy-2-propoxy)methyl]purine (EP A 0217207), such as 2-amino-7-[(1,3-bis-isopropoxy-2-propoxy)methyl]purine and 2-amino-7-[(1,3-dihydroxy-2-propoxy)methyl]purine (DE C 4008858.8), such as 9-[(1,3-dihydroxy-2-propoxy)methyl]guanine (EP A 0049072), such as 9-[(2,3-dihydroxy-1-propoxy)methyl]guanine (W. T. Ashton et al., Biochem. Biophys. Res. Commun. 108, 1716 (1982)) and such as 9-[(2-hydroxyethoxy)methyl]guanine (H. J. Schaeffer et al., Nature 272, 583 (1978)) are active substances with antiviral activity and can be prepared by addition of side chains which are activated in various ways onto the purine system.

The activated side-chain component used to date for introducing the

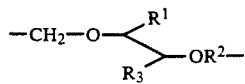

substituents are the halogenomethyl ethers, the methylthiomethyl, methylsulfinylmethyl and methylsulfonylmethyl ethers and the acyloxymethyl ethers of the appropriately substituted alkanols.

All these coupling methods have intrinsic preparative disadvantages: thus, the halogenomethyl ethers are unstable and toxic; the methylthiomethyl, methylsulfinylmethyl and methylsulfonylmethyl ethers provide mercaptans as by-products of the preparation and of the reaction, which give rise to problems in the purification of waste water and exhaust air, and the acyloxymethyl ethers either can be prepared pure only with difficulty and/or undergo a process in their preparation in which dimethyl sulfoxide, which is intrinsically associated with waste water and exhaust air problems, is used.

It has now been found, surprisingly, that symmetrical formaldehyde acetals can be used in the preparation of substituted acyclic nucleosides, and the said problems do not occur therein.

Accordingly, the invention relates to a process for the preparation of substituted acyclic nucleosides, which comprises converting an alcohol of the formula I

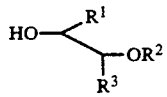

into a formaldehyde acetal of the formula II

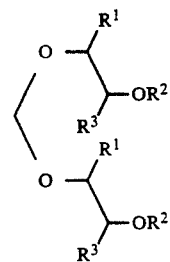

where
- $R^1$ is hydrogen, alkyl, optionally substituted one or more times by halogen, azide, alkoxy, alkenyloxy, alkynyloxy, alkylthio, alkenylthio, alkynylthio, dialkylamino, dialkenylamino, dialkynylamino, benzyloxy, benzylthio, dibenzylamino or phthalimido groups and/or by —P(O)(OR$^4$)(OR$^5$), —P(R$^6$)(O)(OR$^5$), —O—CH$_2$—P(O)(OR$^4$)(OR$^5$) or —O—CH$_2$—P(R$^6$)(O)(OR$^5$) radicals, where $R^4$, $R^5$ and $R^6$ can each, independently of one another, be alkyl;
- $R^2$ is alkyl, benzyl or a —CH$_2$—P(O)(OR$^4$)(OR$^5$) or —CH$_2$—P(R$^6$)(O)(OR$^5$) radical, where $R^4$, $R^5$ and $R^6$ can each, independently of one another, be alkyl;
- $R^3$ is hydrogen, alkyl, optionally substituted one or more times by halogen, azide, alkoxy, alkenyloxy, alkynyloxy, alkylthio, alkenylthio, alkynylthio, dialkylamino, dialkenylamino, dialkynylamino, benzyloxy, benzylthio, dibenzylamino or phthalimido groups and/or by —P(O)(OR$^4$)(OR$^5$), —P(R$^6$)(O)(OR$^5$), —O—CH$_2$—P(O)(OR$^4$)(OR$^5$) or —O—CH$_2$—P(R$^6$)(O)(OR$^5$) radicals, where $R^4$, $R^5$ and $R^6$ can each, independently of one another, be alkyl; and to introduce the group

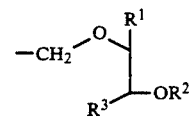

a suitably substituted nitrogen-containing heterocyclic system is reacted with a compound of the formula II.

The process according to the invention is suitable for preparing substituted, nitrogen-containing heterocycles. Examples of these which may be mentioned are: purines such as purine, adenine, 2-chloro-6-aminopurine, hypoxanthine, 6-thiopurine, xanthine, guanine, 2-amino-6-mercaptopurine, 2,6-diaminopurine, 2-aminopurine, 2,6-dihalogenopurine; azapurines such as 8-azapurine, 8-azaadenine, 8-azaguanine; deazapurines such as 1-deazapurines, 3-deazapurines, 7-deazapurines, 9-deazapurines; benzimidazoles; indoles; pyrimidines such as cytosine, 5-halogenocytosines, 4-amino-2-mercaptopyrimidine, uracil, 5-halogenouracils, 4-hydroxy-2-mercaptopyrimidine, thymine, 4-hydroxy-2-mercapto-5-methylpyrimidine, 5-(2-bromovinyl)uracil, 6-substituted pyrimidines such as 6-phenylthiothymine; 2-hydroxypyridines, 4-hydroxypyridines; 1,2,3-triazoles, 1,2,4-triazoles, tetrazoles; imidazoles; pyrroles.

It is particularly important for the preparation of substituted acyclic purine and pyrimidine nucleosides.

The process according to the invention is very particularly important for the preparation of purine nucleosides in which the purine derivative employed is a compound of the formula VI

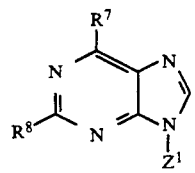

in which $Z^1$ is trialkylsilyl, $R^7$ is halogen and $R^8$ is trialkylsilylated acylamino, and where the reaction leads to a compound of the formula VIa

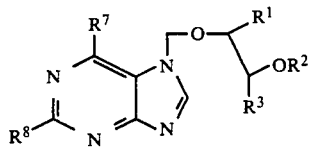

in which the substituents $R^1$–$R^8$ have the abovementioned meanings, and subsequently the substituent $R^8$ can be solvolyzed to the acylamino group.

The process according to the invention is also very particularly important for the preparation of purine nucleosides in which the purine derivative employed is a compound of the formula VII

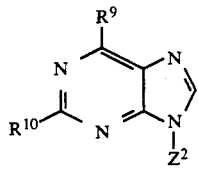

in which $Z^2$ is acyl, $R^9$ is halogen and $R^{10}$ is acylamino, and where the reaction leads to a compound of the formula VIIa

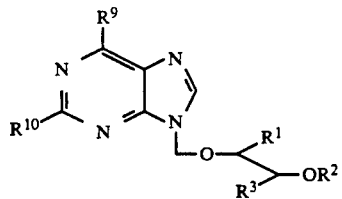

in which the substituents $R^1$–$R^{10}$ have the said meanings, and in which the substituent $R^9$ can be converted into hydrogen by hydrogenolysis and/or the substituent $R^{10}$ can be converted into $NH_2$ by ammonolysis, aminolysis or hydrolysis. The preferred substituents $R^1$–$R^3$ in the described process are those which are indicated hereinafter as preferred for the compounds of the formula II.

The present invention also relates to compounds of the formula II

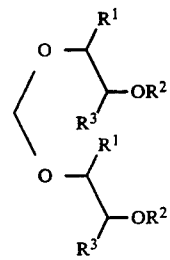

in which the substituents $R^1$–$R^3$ have the abovementioned meanings. Particularly preferred compounds of the formula II are those in which A)

$R^1$ is hydrogen, $C_1$–$C_6$-alkyl, optionally substituted up to twice by halogen, azide, $C_1$–$C_6$-alkoxy, $C_2$–$C_6$-alkenyloxy, $C_2$–$C_6$-alkynyloxy, $C_1$–$C_6$-alkylthio, $C_2$–$C_6$-alkenylthio, $C_2$–$C_6$-alkynylthio, $C_1$–$C_{12}$-dialkylamino, $C_2$–$C_{12}$-dialkenylamino, $C_2$–$C_{12}$-dialkynylamino, benzyloxy, benzylthio, dibenzylamino or phthalimido groups and/or by —P(O)(OR$^4$)(OR$^5$), —P(R$^6$)(O)(OR$^5$), —O—CH$_2$—P(O)(OR$^4$)(OR$^5$) or —O—CH$_2$—P(R$^6$)(O)(OR$^5$) radicals, where $R^4$, $R^5$ and $R^6$ can each, independently of one another, be $C_1$–$C_6$-alkyl, and $R^2$ is $C_1$–$C_6$-alkyl, $C_2$–$C_6$-alkenyl, $C_2$–$C_6$-alkynyl, benzyl or a —CH$_2$—P(O)(OR$^4$)(OR$^5$) or —CH$_2$—P(R$^6$)(O)(OR$^5$) radical, where $R^4$, $R^5$ and $R^6$ can each, independently of one another, be $C_1$–$C_6$-alkyl, and $R^3$ is hydrogen, $C_1$–$C_6$-alkyl, optionally substituted up to twice by halogen, azide, $C_1$–$C_6$-alkoxy, $C_2$–$C_6$-alkenyloxy, $C_2$–$C_6$-alkynyloxy, $C_1$–$C_6$-alkylthio, $C_2$–$C_6$-alkenylthio, $C_2$–$C_6$-alkynylthio, $C_1$–$C_{12}$-dialkylamino, $C_2$–$C_{12}$-dialkenylamino, $C_2$–$C_{12}$-dialkynylamino, benzyloxy, benzylthio, dibenzylamino or phthalimido groups and/or by —P(O)(OR$^4$)(OR$^5$), —P(R$^6$)(O)(OR$^5$), —O—CH$_2$—P(O)(OR$^4$)(OR$^5$) or —O—CH$_2$—P(R$^6$)(O)(OR$^5$) radicals, where $R^4$, $R^5$ and $R^6$ can each, independently of one another, be $C_1$–$C_6$-alkyl.

Very particularly preferred compounds of the formula II are those in which B)

$R^1$ is hydrogen, $C_1$–$C_6$-alkyl, optionally substituted by $C_1$–$C_6$-alkoxy, $C_2$–$C_6$-alkenyloxy, $C_2$–$C_6$-alkynyloxy, $C_1$–$C_6$-alkylthio, benzyloxy, benzylthio, dibenzylamino or phthalimido groups and/or by —P(O)(OR$^4$)(OR$^5$), —P(R$^6$)(O)(OR$^5$), —O—CH$_2$—P(O)(OR$^4$)(OR$^5$) or —O—CH$_2$—P(R$^6$)(O)(OR$^5$) radicals, where $R^4$, $R^5$ and $R^6$ can each, independently of one another, be $C_1$–$C_6$-alkyl, and $R^2$ is $C_1$–$C_6$-alkyl, $C_2$–$C_6$-alkenyl, $C_2$–$C_6$-alkynyl, benzyl or a —CH$_2$—P(O)(OR$^4$)(OR$^5$) radical, where $R^4$ and $R^5$ can each, independently of one another, be $C_1$–$C_6$-alkyl, and $R^3$ is hydrogen, $C_1$–$C_6$-alkyl, optionally substituted by $C_1$–$C_6$-alkoxy, $C_2$–$C_6$-alkenyloxy, $C_2$–$C_6$-alkynyloxy, $C_1$–$C_6$-alkylthio, benzyloxy, benzylthio, dibenzylamino or phthalimido groups and/or by —P(O)(OR$^4$)(OR$^5$), —P(R$^6$)(O)(OR$^5$), —O—CH$_2$—P(O)(OR$^4$)(OR$^5$) or —O—CH$_2$—P(R$^6$)(O)(OR$^5$) radicals, where $R^4$, $R^5$ and $R^6$ can each, independently of one another, be $C_1$–$C_6$-alkyl, especially compounds of the formula II in which C)

$R^1$ is hydrogen, $C_1-C_6$-alkoxymethyl, $C_2-C_6$-alkenyloxymethyl, $C_2-C_6$-alkynyloxymethyl, benzyloxymethyl, $-CH_2-P(O)(OR^4)(OR^5)$, $-CH_2-CH_2-P(O)(OR^4)(OR^5)$, $-CH_2-P(R^6)(O)(OR^5)$, $-CH_2-CH_2-P(R^6)(O)(OR^5)$, $-CH_2-O-CH_2-P(O)(OR^4)(OR^5)$ or $-CH_2-O-CH_2-P(R^6)(O)(OR^5)$, where $R^4$, $R^5$ and $R^6$ can each, independently of one another, be $C_1-C_6$-alkyl, and $R^2$ is $C_1-C_6$-alkyl, $C_2-C_6$-alkenyl, $C_2-C_6$-alkynyl or benzyl, and $R^3$ is hydrogen, $C_1-C_6$-alkoxymethyl, $C_2-C_6$-alkenyloxymethyl, $C_2-C_6$-alkynyloxymethyl, benzyloxymethyl, $-CH_2-P(O)(OR^4)(OR^5)$, $-CH_2-CH_2-P(O)(OR^4)(OR^5)$, $-CH_2-P(R^6)(O)(OR^5)$, $-CH_2-CH_2-P(R^6)(O)(OR^5)$, $-CH_2-O-CH_2-P(O)(OR^4)(OR^5)$ or $-CH_2-O-CH_2-P(R^6)(O)(OR^5)$, where $R^4$, $R^5$ and $R^6$ can each, independently of one another, be $C_1-C_6$-alkyl.

The alkyl, alkenyl and alkynyl groups mentioned as substituents can be straight-chain, branched or cyclic. Examples of suitable alkyl groups are methyl, ethyl, propyl, isopropyl, cyclopentyl, cyclohexyl; examples of suitable alkenyl groups are propenyl, 3-isobutenyl, 3-cyclohexenyl; examples of suitable alkynyl groups are 3-propynyl or 4-butynyl.

The said acyl groups can be straight-chain, branched, cycloaliphatic or aromatic. Examples of suitable acyl groups are acetyl, propionyl, butyryl, isobutyryl, valeroyl, cyclopentanoyl, cyclohexanoyl, benzoyl or 4-methylbenzoyl.

The compounds of the formula II can have one or more chiral centers. The compounds are usually in the form of racemates; preparation or isolation of the pure enantiomers is possible. The invention therefore relates both to the pure enantiomers and to mixtures thereof such as, for example, the relevant racemate.

The present invention additionally relates to a process for the preparation of compounds of the formula II, which comprises reacting the compounds of the formula I with paraformaldehyde, formaldehyde dimethyl acetal or formaldehyde diethyl acetal in the presence of a catalyst. To carry out the process, an alkanol of the formula I, paraformaldehyde or formaldehyde dimethyl acetal or formaldehyde diethyl acetal, preferably formaldehyde, are mixed with a solvent such as, for example, toluene, but preferably without a solvent, with an inorganic protonic acid catalyst such as concentrated sulfuric acid or with an organic protonic acid catalyst such as para-toluenesulfonic acid or with a cation exchanger or with a Lewis acid catalyst such as anhydrous calcium chloride or iron trichloride, preferably para-toluenesulfonic acid, and heated under pressure in an autoclave, but preferably under atmospheric pressure, with stirring at 50° to 200° C., preferably at 100° C., for 1 to 24 hours, preferably for 3-7 hours. The water formed in this reaction can be removed by distillation, where appropriate azeotropically. It is alternatively possible to add a dehydrating agent such as activated 4 Angstrom molecular sieves. The most favorable molar ratio of formaldehyde (equivalent):alkanol is 0.2:1.0 to 1.5:1.0, preferably 0.33:1.0.

Similar processes are described, for example, in Houben-Weyl, Methoden der organischen Chemie (Methods of Organic Chemistry) Volume VI/3, pp. 203 et seq., Georg Thieme Verlag, Stuttgart, 1965.

The reaction mixture can be worked up by conventional methods. The working up is carried out in such a way, for example, that the reaction mixture is fractionally distilled in vacuo, but preferably in such a way that the reaction mixture is dissolved in a dialkyl ether, extracted by shaking several times with water and dried over sodium sulfate before it is fractionally distilled in vacuo. The fractional distillation not only yields the symmetrical formaldehyde acetal of the formula II but also recovers unreacted alkanol of the formula I.

The present invention also relates to a process for the preparation of acyclic nucleosides substituted by a

group, which comprises reacting a compound of the formula II with a suitable nitrogen-containing heterocycle, where the substituents $R^1-R^3$ have the abovementioned meanings.

The present invention particularly relates to a process for the preparation of the abovementioned compounds of the formula VIa, wherein the purine derivative employed is a compound of the abovementioned formula VI in which $Z^1$ is trialkylsilyl, especially trimethylsilyl, $R^7$ is halogen, especially chlorine, and $R^8$ is trialkylsilylated acylamino, preferably trimethylsilylated benzoylamino or trimethylsilylated $C_1-C_8$ aliphatic acylamino, especially trimethylsilylated acetamido.

The purine derivative is reacted with a symmetrical formaldehyde acetal according to the invention, of the formula II, whose radicals $R^1$, $R^2$ and $R^3$ are as described above under A), B) or C), preferably in an aprotic solvent such as benzene, toluene, xylene, acetonitrile, dichloromethane or 1,2-dichloroethane or mixtures thereof in the presence of an acid catalyst, preferably of a Lewis acid catalyst such as aluminum trichloride, aluminum sulfate, iron trichloride, gallium trichloride, tin tetrachloride, titanium tetrachloride, boron trifluoride, cesium fluoride, cesium sulfate or trialkylsilyl trifluoromethanesulfonates, especially trimethylsilyl trifluoromethanesulfonate, where the amounts of these catalyst reagents are 0.1-10, preferably 0.8-7 equivalents based on the amount of the symmetrical formaldehyde acetal employed in each case, at temperatures between $-70°$ C. and $+80°$ C., preferably between $-40°$ C. and $+30°$ C., for 2 to 24 hours, preferably for 2 to 6 hours.

This process yields with high regioselectivity, as a rule $>>9:1$, preferentially the N7 isomer of the particular purine derivative of the formula VIa with $R^7$=acylamino after the labile trialkylsilyl protective group has been removed by mild solvolysis with water, with aqueous or alcoholic ammonia or with aqueous sodium bicarbonate solution or by alcoholysis.

The products of the formula VIa can be reacted further to other purine derivatives as described in German Patent Application P 40 08 858.8.

The present invention furthermore relates to a process for the preparation of the abovementioned compounds of the formula VIIa, wherein the purine derivative employed is a compound of the abovementioned formula VII in which $Z^2$ is benzoyl or $C_1-C_8$ aliphatic or cycloaliphatic acyl, especially acetyl, $R^9$ is halogen, especially chlorine, and $R^{10}$ is benzoyl- or $C_1-C_8$ aliphatic or cycloaliphatic acylamino, especially acetamido. The purine derivative is reacted with a symmetrical formaldehyde acetal according to the invention, of the formula II, whose radicals $R^1$, $R^2$ and $R^3$ are as described above under A), B) or C), preferably in a polar aprotic solvent such as sulfolane, dimethyl sulfoxide, dimethylacetamide, dimethylformamide or N-methyl-2-pyrrolidone or mixtures thereof, preferably N-methyl-2-pyrrolidone, in the presence of a protic acid catalyst such as para-toluenesulfonic acid or bis(4-nitrophenyl) phosphate, preferably a Lewis acid catalyst such as aluminum trichloride, aluminum sulfate, iron trichloride, gallium trichloride, tin tetrachloride, titanium tetrachloride, cesium fluoride, cesium sulfate, boron trifluoride or boron trifluoride-dialkyl ether complex, particularly preferably aluminum sulfate or boron trifluoride-dialkyl ether complex, where the amounts of these catalyst reagents are 0.1-10, 0.2-5 equivalents based on the amount of the symmetrical formaldehyde acetal employed in each case, at temperatures between 0° C. and 200° C., preferably between 70° C. and 120° C., for 2-24 hours, preferably for 2-8 hours. This process yields with high regioselectivity, usually $>>9:1$, preferentially the N9 isomer of the particular purine derivative of the formula VIIa.

The present patent application additionally relates to compounds of the formula

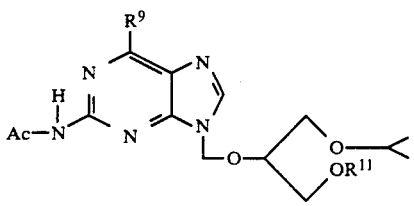

in which $R^9$ is halogen or hydrogen and $R^{11}$ is isopropyl or benzyl.

These compounds have antiviral activity and are, furthermore, important for the preparation of other purine nucleosides.

The present invention is explained in more detail by the exemplary embodiments which follow.

EXAMPLE 1.

Compound of the formula II in which $R^1$ is isopropoxymethyl, $R^2$ is isopropyl and $R^3$ is hydrogen:

105.6 g (0.6 mol) of 1,3-bis-isopropoxy-2-propanol are heated with 6 g (0.2 mol) of paraformaldehyde and 0.25 g of para-toluenesulfonic acid with stirring slowly to 100° C. The reaction mixture is stirred at this temperature for 4 hours. The cooled reaction mixture is dissolved in diethyl ether and extracted by shaking several times with water, and the organic phase is then dried over sodium sulfate. Fractional distillation yields 58.5 g of initial alcohol of boiling point 60° C. under 0.7 mm Hg and 46.5 g (61.5% based on paraformaldehyde) of formaldehyde bis-(1,3-bis-isopropoxy-2-propyl) acetal of boiling point 130°-134° C. under 0.7 mm Hg. 1H NMR (60 MHz, CDCl$_3$), δ [ppm]: 4.93 (s, 2H), 4.13-3.33 (m, 14H), 1.15 (d, 24H).

The following can be prepared in a similar manner
formaldehyde bis-(1,3-bis-methoxy-2-propyl) acetal
formaldehyde bis-(1,3-bis-ethoxy-2-propyl) acetal
formaldehyde bis-(1,3-bis-propoxy-2-propyl) acetal
formaldehyde bis-(1,3-bis-butoxy-2-propyl) acetal
formaldehyde bis-(1,3-bis-cyclopentyloxy-2-propyl)acetal
formaldehyde bis-(1,3-bis-cyclohexyloxy-2-propyl) acetal
formaldehyde bis-[1,3-bis(2-butyloxy)-2-propyl] acetal
formaldehyde bis-[1,3-bis(2-methyl-3-propyloxy)-2-propyl] acetal
formaldehyde bis-(1-isopropoxy-3-methoxy-2-propyl) acetal
formaldehyde bis-(1-isopropoxy-3-ethoxy-2-propyl) acetal
formaldehyde bis-(1-isopropoxy-3-propoxy-2-propyl) acetal
formaldehyde bis-(1-isopropoxy-3-butoxy-2-propyl) acetal
formaldehyde bis-(1-isopropoxy-3-cyclopentyloxy-2-propyl) acetal
formaldehyde bis-(1-isopropoxy-3-cyclohexyloxy-2-propyl) acetal
formaldehyde bis-[1,3-bis(3-propenyloxy)-2-propyl]acetal
formaldehyde bis-[1-isopropoxy-3-(3-propenyloxy)-2-propyl] acetal
formaldehyde bis-(1,3-bis-benzyloxy-2-propyl) acetal
formaldehyde bis-(1-benzyloxy-3-methoxy-2-propyl) acetal
formaldehyde bis-(1-benzyloxy-3-ethoxy-2-propyl) acetal
formaldehyde bis-(1-benzyloxy-3-propoxy-2-propyl) acetal
formaldehyde bis-(1-benzyloxy-3-isopropoxy-2-propyl) acetal
formaldehyde bis-(1-isopropoxy-3-ethylthio-2-propyl) acetal
formaldehyde bis-(1-benzyloxy-3-ethylthio-2-propyl) acetal
formaldehyde bis-(1-isopropoxy-3-methylthio-2-propyl) acetal
formaldehyde bis-(1-benzyloxy-3-methylthio-2-propyl) acetal
formaldehyde bis-(1-isopropoxy-3-N-phthalimido-2-propyl) acetal
formaldehyde bis-(1-benzyloxy-3-N-phthalimido-2-propyl) acetal
formaldehyde bis-[1-isopropoxy-3-((O,O-diisopropyl)-phosphonylmethoxy)-2-propyl] acetal
formaldehyde bis-[1-isopropoxy-4-((O,O-diisopropyl)-phosphonyl)-2-butyl] acetal
formaldehyde bis-[1-isopropoxy-4-(isopropoxy(methyl)phosphoryl)-2-butyl] acetal
formaldehyde bis-(1-isopropoxy-2-benzyloxy-3-propyl) acetal
formaldehyde bis-(1-isopropoxy-2-methoxy-3-propyl) acetal
formaldehyde bis-(1-isopropoxy-2-ethoxy-3-propyl) acetal
formaldehyde bis-(1-isopropoxy-2-propoxy-3-propyl) acetal
formaldehyde bis-(1,2-bis-isopropoxy-3-propyl) acetal
formaldehyde bis-(1,2-bis-benzyloxy-3-propyl) acetal
formaldehyde bis-(1-benzyloxy-2-methoxy-3-propyl) acetal
formaldehyde bis-(1-benzyloxy-2-isopropoxy-3-propyl) acetal
formaldehyde bis-(2-benzyloxy-1-ethylthio-3-propyl) acetal
formaldehyde bis-(2-methoxy-1-ethylthio-3-propyl) acetal formaldehyde bis-(2-isopropoxy-1-ethylthio-3-propyl) acetal
formaldehyde bis-(2-benzyloxy-1-N-phthalimido-3-propyl) acetal
formaldehyde bis-[2-benzyloxy-1-((O,O-diisopropyl)-phosphonylmethoxy)-3-propyl]acetal
formaldehyde bis-[1-isopropoxy-2-((O,O-diisopropyl)-phosphonylmethoxy)-3-propyl]acetal
formaldehyde bis-(2-isopropoxy-1-ethyl) acetal
formaldehyde bis-(2-methoxy-1-ethyl) acetal
formaldehyde bis-(2-ethoxy-1-ethyl) acetal
formaldehyde bis-(2-propoxy-1-ethyl) acetal
formaldehyde bis-(2-butoxy-1-ethyl) acetal
formaldehyde bis-(2-benzyloxy-1-ethyl) acetal
formaldehyde bis-(2-ethylthio-1-ethyl) acetal
formaldehyde bis-[2-((O,O-diisopropyl)phosphonylmethoxy)-1-ethyl] acetal
formaldehyde bis-[2-(isopropoxy(methyl)phosphoryl)-1-ethyl] acetal

EXAMPLE 2.1.

Compound of the formula VIa in which $R^7$ is chlorine, $R^8$ is acetamido, $R^1$ is isopropoxymethyl, $R^2$ is isopropyl and $R^3$ is hydrogen:

6.9 g (0.033 mol) of 2-acetamido-6-chloropurine are reacted in 28 ml of dry xylene with 28 ml of hexamethyldisilazane (HMDS) and 0.2 g of ammonium sulfate at the reflux temperature for 3 hours, and give a compound of the formula VI in which $R^7$ is chlorine, $R^8$ is trimethylsilylated acetamido and $Z^1$ is trimethylsilyl. The solvent and excess HMDS are removed from the reaction mixture, which is dissolved in 85 ml of dry 1,2-dichloroethane and added at $-30°$ C. to a solution of 11.96 g (0.033 mol) of formaldehyde bis-(1,3-bis-isopropoxy-2-propyl) acetal (compound from Example 1) in 85 ml of dry 1,2-dichloroethane. Then, at $-30°$ C., 5 ml (0.026 mol) of trimethylsilyl trifluoromethanesulfonate are slowly added, and the reaction mixture is stirred at $-30°$ C. for 2 hours. The mixture is then stirred into 500 ml of ice-water and filtered. The residue is washed with 50 ml of 1,2-dichloroethane. The organic phase is separated off, and the aqueous phase is extracted by shaking 3× with 100 ml of 1,2-dichloroethane. The combined organic phases are extracted by shaking 1× with 100 ml of water, 2× with 100 ml of dilute sodium bicarbonate solution and again with 100 ml of water, dried over sodium sulfate, filtered and concentrated. The residue, whose HPLC analysis indicates a ratio of N7:N9 substitution of 10:1, is purified by chromatography on silica gel with ethyl acetate/methanol 15/1 and yields 7.64 g (58% of theory) of 2-acetamido-6-chloro-7-[(1,3-bis-isopropoxy-2propoxy)-methyl]purine of melting point 73°–75° C. 1H NMR (270 MHz, d6-DMSO), δ [ppm]: 10.68 (s, 1H), 8.84 (s, 1H), 5.81 (s, 2H), 3.71 (m, 1H), 3.46–3.24 (m, 6H), 2.18 (s, 3H), 0.90 (m, 12H).

EXAMPLE 2.2.

Compound of the formula VIa in which $R^7$ is chlorine, $R^8$ is acetamido, $R^1$ is hydrogen, $R^2$ is isopropyl and $R^3$ is hydrogen:

27.9 g (0.132 mol) of 2-acetamido-6-chloropurine are converted as described in Example 2.1. into the bis-trimethylsilyl compound of the formula VI where $R^7$=chlorine, $R^8$=trimethylsilylated acetamido and $Z^1$=trimethylsilyl, dissolved in 340 ml of 1,2-dichloroethane and added at $-30°$ C. to a solution of 21.7 g (0.096 mol) of formaldehyde bis-(2-isopropoxy-1-ethyl) acetal (compound of the formula II in which $R^1$ is hydrogen, $R^2$ is isopropyl and $R^3$ is hydrogen) in 340 ml of 1,2-dichloroethane. While stirring at $-30°$ C., 20 ml (0.104 mol) of trimethylsilyl trifluoromethanesulfonate are added dropwise. After 2 hours at $-30°$ C., the reaction mixture is worked up as in Example 2.1. and yields 15.8 g (50% of theory based on formaldehyde acetal of the formula II) of 2-acetamido-6-chloro-7-(2-isopropoxyethoxymethyl)purine with melting point 116°–117° C. 1H NMR (270 MHz, d6-DMSO), δ [ppm]: 10.51 (s, 1H), 8.86 (s, 1H), 5.78 (s, 2H), 3.60 (m, 2H), 3.50–3.40 (m, 3H), 2.19 (s, 3H), 0.97 (d,6H).

EXAMPLE 2.3.

Compound of the formula VIa in which $R^7$ is chlorine, $R^8$ is acetamido, $R^1$ is hydrogen, $R^2$ is benzyl and $R^3$ is isopropoxymethyl:

Analogous reaction with formaldehyde di-(2-benzyloxy-3-isopropoxy-1-propyl) acetal (compound of the formula II in which $R^1$ is hydrogen, $R^2$ is benzyl and $R^3$ is isopropoxymethyl) gives a 51% yield of 2-acetamido-6-chloro-7-[(2-benzyloxy-3-isopropoxy-1-propoxy)methyl]purine as a yellowish syrup. 1H NMR (60 MHz, d6-DMSO), δ [ppm]: 10.73 (s, 1H), 8.90 (s, 1H), 7.28 (s, 5H), 5.80 (s, 2H), 4.52 (s, 2H), 3.65–3.20 (m, 6H), 2.20 (s, 3H), 0.92 (d, 6H).

EXAMPLE 3.1.

Compound Of the formula VIIa in which $R^9$ is chlorine, $R^{10}$ is acetamido, $R^1$ is isopropoxymethyl, $R^2$ is isopropyl and $R^3$ is hydrogen:

4.5 g (0.011 mol) of formaldehyde bis-(1,3-bis-isopropoxy-2-propyl) acetal (compound of the formula II in which $R^1$ is isopropoxymethyl, $R^2$ is isopropoxy and $R^3$ is hydrogen) are added to a solution of 2.54 g (0.01 mol) of $N^2,N^9$-diacetyl-6-chloropurine (compound of the formula VII in which $R^9$ is chlorine, $R^{10}$ is acetamido and $Z^2$ is acetyl) in 25 ml of dry N-methyl-2-pyrrolidone (NMP). While stirring, 2.84 g (2.5 ml, 0.01 mol) of a 50% strength boron trifluoride etherate solution are added dropwise, and the mixture is then stirred at 100° C. for 4 hours. The cooled reaction mixture is stirred into a mixture of ice, water and dichloromethane, the organic phase is separated off and the aqueous phase is extracted 3× with dichloromethane, after which the combined organic phases are extracted by shaking with water, dried over sodium sulfate and the solvent is removed. HPLC analysis of the crude product shows an N9:N7 isomer ratio of 85:1.7. Stirring the crude product with diisopropyl ether yields 2.5 g (62.6% of theory) of 2-acetamido-6-chloro-9-[(1,3-bis-isopropoxy-2-propoxy)methyl]purine of melting point 106° C. 1H NMR (60 MHz, d6-DMSO), δ [ppm]: 10.83 (s, 1H), 8.65 (s, 1H), 5.70 (s, 2H), 4.03–3.67 (m, 1H), 3.63–3.17 (m, 6H), 2.22 (s, 3H), 0.90 (d, 12H).

EXAMPLE 3.2.

The compound of Example 3.1. can also be obtained by treating 0.01 mol of $N^2,N^9$-diacetyl-6-chloropurine with 0.011 mol of formaldehyde bis-(1,3-bis-isopropoxy-2propyl) acetal and 0.1 mol of anhydrous aluminum sulfate in dry NMP at 100° C. for six hours. HPLC analysis of the crude product shows an N9:N7 isomer ratio of 73.6:8.2. 2-Acetamido-6-chloro-9-[(1,3-bis-isopropoxy-2-propoxy)methyl]purine is isolated in 61% yield.

EXAMPLE 3.3.

The compound of Example 3.1. can furthermore be obtained by stirring 0.01 mol of $N^2,N^9$-diacetyl-6-chloropurine with 0.011 mol of formaldehyde bis-(1,3-bis-isopropoxy-2-propyl) acetal in anhydrous dimethylformamide with 0.05 mol of tin tetrachloride at 100° C. for eight hours. HPLC analysis of the crude product shows an N9:N7 isomer ratio of 93.2:2.4. The yield of 2-acetamido-6-chloro-9-[(1,3-bis-isopropoxy-2-propoxy)methyl]purine is 64%.

EXAMPLE 3.4.

Carrying out the reaction as in Example 3.3. but with NMP in place of dimethylformamide as solvent yields 95.5% N9 isomer and 2.4% N7 isomer according to HPLC analysis. The yield of 2-acetamido-6-chloro-9-[(1,3-bis-isopropoxy-2propoxy)methyl]purine is 75%.

EXAMPLE 3.5.

Compound of the formula VIIa in which $R^9$ is chlorine, $R^{10}$ is acetamido, $R^1$ is hydrogen, $R^2$ is isopropyl and $R^3$ is hydrogen:

Reaction of 12.7 g (0.05 mol) of $N^2,N^9$-diacetyl-6-chloropurine with 22.5 g (0.55 mol) of formaldehyde bis-(2-isopropoxy-1-ethyl) acetal (compound of the formula II in which $R^1$ is hydrogen, $R^2$ is isopropyl and $R^3$ is hydrogen) and 65 g (0.25 mol) of tin tetrachloride in 125 ml of NMP yields, after 4 hours at 100° C., after working up as described above and after purification by chromatography on silica gel with ethyl acetate/methanol 9/1, 9.5 g (58% of theory) of 2-acetamido-6-chloro-9-[(2-isopropoxyethoxy)methyl]purine of melting point 135°-137° C. 1H NMR (270 MHz, d$_6$-DMSO), δ [ppm]: 10.84 (s, 1H), 8.64 (s, 1H), 5.60 (s, 2H), 3.69-3.65 (m, 2H), 3.54-3.41 (m, 3H), 2.21 (s, 3H) 0.99 (d, 6H).

EXAMPLE 3.6.

Compound of the formula VIIa in which $R^9$ is chlorine, $R^{10}$ is acetamido, $R^1$ is hydrogen, $R^2$ is benzyl and $R^3$ is isopropoxymethyl:

Reaction in analogy to Example 3.5. with formaldehyde bis-(2-benzyloxy-3-isopropoxy-1-propyl) acetal (compound of the formula II in which $R^1$ is hydrogen, $R^2$ is benzyl and $R^3$ is isopropoxy) gives a 53% yield of 2-acetamido-6-chloro-9-[(2-benzyloxy-3-isopropoxy-1-propoxy)methyl]purine of melting point 87°-89° C.

1H NMR (60 MHz, d$_6$-DMSO), δ [ppm]: 10.87 (s, 1H), 8.67 (s, 1H), 7.28 (s, 5H), 5.63 (s, 2H), 4.51 (s, 2H), 3.73-3.22 (m, 6H), 2.20 (s, 3H), 0.95 (d, 6H).

EXAMPLE 3.7.

Compound of the formula VIIa in which $R^9$ is chlorine, $R^{10}$ is acetamido, $R^1$ is benzyloxymethyl, $R^2$ is isopropyl and $R^3$ is hydrogen:

Reaction in analogy to Example 3.1. with formaldehyde bis-(1-benzyloxy-3-isopropoxy-2-propyl) acetal (compound of the formula II in which $R^1$ is benzyloxymethyl, $R^2$ is isopropyl and $R^3$ is hydrogen) yields 2-acetamido-6-chloro-9-[(1-benzyloxy-3-isopropoxy-2-propoxy)methyl]purine. Oil, 1H NMR (270 MHz, d$_6$-DMSO), δ [ppm]: 10.82 (s, 1H), 8.63 (s, 1H), 7.33-7.14 (m, 5H), 5.69 (s, 2H), 4.39 (s, 2H), 4.04 (m, 1H), 3.49-3.25 (m, 5H), 2.20 (s, 3H), 0.91 (2d, 6H).

Compounds of the formula VIIa in which $R^9$ is halogen, preferably chlorine, $R^{10}$ is benzoyl- or $C_1$-$C_8$ aliphatic or cycloaliphatic acylamino, preferably acetamido, and $R^1$, $R^2$ and $R^3$ are as defined above, can be converted into compounds of the formula VIIa in which $R^9$ is hydrogen, $R^{10}$ is benzoyl- or $C_1$-$C_8$ aliphatic or cycloaliphatic acylamino, preferably acetamido, or amino and $R^1$ is preferably isopropoxymethyl, $R^2$ is preferably isopropyl and $R^3$ is preferably hydrogen. The preferred process comprises the hydrogenolysis of the group $R^9$ and the ammonolysis, aminolysis or hydrolysis of the group $R^{10}$ of compounds of the formula VIIa in which $R^1$, $R^2$ and $R^3$ are as defined above.

EXAMPLE 4.1.

Conversion of a compound of the formula VIIa in which $R^9$ is chlorine, $R^{10}$ is acetamido, $R^1$ is isopropoxymethyl, $R^2$ is isopropoxy and $R^3$ is hydrogen, into a compound of the formula VIIa in which $R^9$ is hydrogen, $R^{10}$ is acetamido, $R^1$ is isopropoxymethyl, $R^2$ is isopropyl and $R^3$ is hydrogen: 10.5 g (0.026 mol) of the compound of Example 3.1. are dissolved in 220 ml of methanol, and 2.2 g of palladium on carbon (10%) and 7 ml of triethylamine are added and the mixture is treated with hydrogen at room temperature. After the theoretical amount of hydrogen has been absorbed, the catalyst is removed by filtration, the residue is washed with methanol, and the solvent is removed from the solution. The crystalline residue is stirred in ethyl acetate, filtered, and the residue is washed with ethyl acetate. Solvent is removed from the filtrate, and the residue is purified by chromatography on silica gel with ethyl acetate/methanol 9/1. 8.9 g (93.8% of theory) of 2-acetamido-9-[(1,3-bis-isopropoxy-2-propoxy)methyl]purine of melting point 85°-86° C. are obtained. 1H NMR (60 MHz, d$_6$-DMSO), δ [ppm]: 10.60 (s, 1H), 9.03 (s, 1H), 8.60 (s, 1H), 5.70 (s, 2H), 3.93 (m, 1H), 3.67-3.22 (m, 6H), 2.25 (s, 3H), 0.93 (d, 12H).

EXAMPLE 4.2.

Compound of the formula VIIa in which $R^9$ is hydrogen, $R^{10}$ is acetamido, $R^1$ is benzyloxymethyl, $R^2$ is isopropyl and $R^3$ is hydrogen:

2-Acetamido-9-[(1-benzyloxy-3-isopropoxy-2-propoxy)methyl]purine can be obtained from the compound of Example 3.7. in a manner analogous to that described in Example 4.1. Oil, 1H NMR (270 MHz, d$_6$-DMSO), δ [ppm]: 10.58 (s, 1H), 8.98 (s, 1H), 8.57 (s, 1H), 7.34-7.17 (m, 5H), 5.69 (s, 2H), 4.39 (s, 2H), 4.03 (m, 1H), 3.49-3.25 (m, 5H), 2.21 (s, 3H), 0.92 (d, 6H).

EXAMPLE 4.3.

Conversion of a compound of the formula VIIa in which $R^9$ is hydrogen, $R^{10}$ is acetamido, $R^1$ is isopropoxymethyl, $R^2$ is isopropyl and $R^3$ is hydrogen into a compound of the formula VIIa in which $R^9$ is hydrogen, $R^{10}$ is amino, $R^1$ is isopropoxymethyl, $R^2$ is isopropyl and $R^3$ is hydrogen:

17 g (0.047 mol) of the compound of Example 4.1. in 85 ml of methanol and 85 ml of 40% strength aqueous methylamine solution are heated under reflux for two hours. Methanol is removed from the cooled solution, which is then treated with active carbon, filtered and neutralized with dilute acetic acid, saturated with sodium chloride and extracted several times by shaking with dichloromethane. The organic phase is washed with saturated brine, dried over sodium sulfate and, after the solvent has been removed, purified by chromatography on silica gel with ethyl acetate/methanol 9/1. 13.2 g (86.9% of theory) of 2-amino-9-[(1,3-diisopropoxy-2-propoxy)methyl]purine of melting point 89°–90° C. are obtained in this way.

1H NMR (270 MHz, d$_6$-DMSO), δ [ppm]: 8.59 (s, 1H), 8.16 (s, 1H), 6.52 (s, 2H), 5.52 (s, 2H), 3.80 (m, 1H), 3.49–3.21 (m, 6H), 0.97 (m, 12H).

EXAMPLE 4.4.

Compound of the formula VIIa in which R$^9$ is hydrogen, R$^{10}$ is amino, R$^1$ is benzyloxymethyl, R$^2$ is isopropyl and R$^3$ is hydrogen:

2-Amino-9-[(1-benzyloxy-3-isopropoxy-2-propoxy)-methyl]purine can be obtained from the compound of Example 4.2. in a manner analogous to that described in Example 4.3.

I claim:

1. A process for the preparation of substituted acyclic nucleosides, which comprises converting an alcohol of the formula I

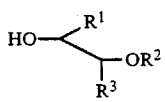

into a formaldehyde acetal of the formula II

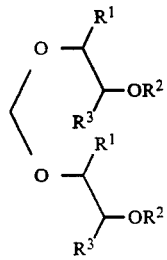

where
R$^1$ is hydrogen, alkyl, optionally substituted one or more times by halogen, azide, alkoxy, alkenyloxy, alkynyloxy, alkylthio, alkenylthio, alkynylthio, dialkylamino, dialkenylamino, dialkynylamino, benzyloxy, benzylthio, dibenzylamino or phthalimido groups and/or by —P(O)(OR$^4$)(OR$^5$), —P(R$^6$)(O)(OR$^5$), —O—CH$_2$—P(O)(OR$^4$)(OR$^5$) or —O—CH$_2$P(R$^6$)(O)(OR$^5$) radicals, where R$^4$, R$^5$ and R$^6$ can each, independently of one another, be C$_1$–C$_6$-alkyl;
R$^2$ is alkyl, benzyl or a —CH$_2$—P(O)(OR$^4$)(OR$^5$) or —CH$_2$—P(R$^6$)(O)(OR$^5$) radical, where R$^4$, R$^5$ and R$^6$ can each, independently of one another, by C$_1$–C$_6$-alkyl;
R$^3$ is hydrogen, alkyl, optionally substituted one or more times by halogen, azide, alkoxy, alkenyloxy, alkynyloxy, alkylthio, alkenylthio, alkynylthio, dialkylamino, dialkenylamino, dialkynylamino, benzyloxy, benzylthio, dibenzylamino or phthalimido groups and/or by —P(O)(OR$^4$)(OR$^5$), —P(R$^6$)(O)(OR$^5$), —O—CH$_2$—P(O)(OR$^4$)(OR$^5$) or —O—CH$_2$—P(R$^6$)(O)(OR$^5$) radicals, where R$^4$, R$^5$ and R$^6$ can each, independently of one another, be C$_1$–C$_6$-alkyl;
and to introduce the group

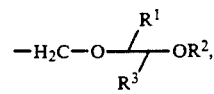

a suitably substituted nitrogen-containing heterocyclic system selected from the group consisting of a purine compound selected from purine, adenine, 2-chloro-6-aminopurine, hypoxanthine, 6-thiopurine, xanthine, guanine, 2-amino-6-mercaptopurine, 2,6-diaminopurine, 2-aminopurine and 2,6-dihalogenopurine; and azapurine selected from 8-azapurine, 8-azaadenine and 8-azaguanine; a deazapurine selected from a 1-deazapurine, a 3-deazapurine, a 7-deazapurine and a 9-deazapurine; a benzimidazole; an indole; a pyrimidine selected from cytosine, a 5-halogenocytosine, 4-amino-2-mercaptopyrimidine, uracil, a 5-halogenouracil, 4-hydroxy-2-mercaptopyrimidine, thymine, 4-hydroxy-2-mercapto-5-methyl-pyrimidine, 5-(2-bromovinyl)uracil and 6-phenylthiothymine; a pyridine compound selected from 2-hydroxypyridine and 4-hydroxypyridine; and an azole compound selected from 1,2,3-triazole, 1,2,4-triazole, a tetrazole, an imidazole and pyrrole is reacted with a compound of the formula II.

2. The process as claimed in claim 1, wherein the nitrogen-containing heterocyclic system is said purine compound.

3. The process as claimed in claim 2 wherein the purine compound employed is a compound of the formula VI

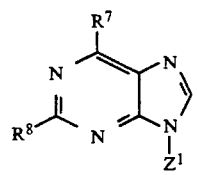

in which Z$^1$ is trialkylsilyl, R$^7$ is halogen and R$^8$ is trialkylsilylated acylamino.

4. The process as claimed in claim 1 or 2, wherein the purine compound employed is a compound of the formula VII

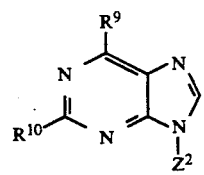

in which Z$^2$ is acyl, R$^9$ is halogen and R$^{10}$ is acylamino and, after the reaction, where appropriate the substituent R$^9$ is converted into H by hydrogenolysis and/or the substituent R$^{10}$ is converted into NH$_2$ by ammonolysis, aminolysis or hydrolysis.

5. A compound of the formula II

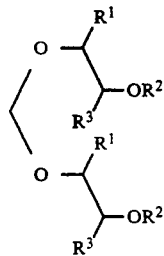

where the substituents $R^1$–$R^3$ have the meaning specified in claim 1.

6. A process for the preparation of compounds of the formula II as claimed in claim 5, which comprises reacting compounds of the formula I

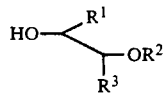

where $R^1$–$R^3$ have the meanings specified in claim 1, with paraformaldehyde, formaldehyde dimethyl acetal or formaldehyde diethyl acetal in the presence of a catalyst.

7. A process for the preparation of acyclic nucelosides substituted by a group, which comprises reacting a compound of the formula II

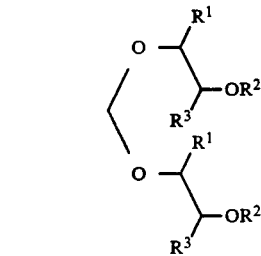

with a suitable nitrogen-containing heterocyclic system as claimed in claim 1, where the substituents $R^1$–$R^3$ have the meanings as claimed in claim 1.

8. A compound of the formula

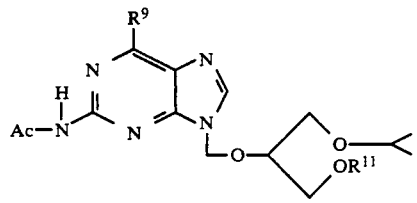

in which $R^9$ is halogen or hydrogen and $R^{11}$ is isopropyl or benzyl.

* * * * *